US008135456B2

(12) United States Patent
Haluska

(10) Patent No.: US 8,135,456 B2
(45) Date of Patent: *Mar. 13, 2012

(54) DEVICE AND METHOD FOR DETECTING ATRIAL FIBRILLATION

(75) Inventor: Jeffrey A. Haluska, Budd Lake, NJ (US)

(73) Assignee: Pacesetter, Inc., Sylmar, CA (US)

( * ) Notice: Subject to any disclaimer, the term of this patent is extended or adjusted under 35 U.S.C. 154(b) by 235 days.

This patent is subject to a terminal disclaimer.

(21) Appl. No.: 12/427,685

(22) Filed: Apr. 21, 2009

(65) Prior Publication Data
US 2009/0270749 A1 Oct. 29, 2009

Related U.S. Application Data

(60) Provisional application No. 61/048,129, filed on Apr. 25, 2008.

(51) Int. Cl.
A61B 5/04 (2006.01)

(52) U.S. Cl. ...................................... 600/518

(58) Field of Classification Search .................. 600/508, 600/509, 515, 518, 521; 607/5, 25
See application file for complete search history.

(56) References Cited

U.S. PATENT DOCUMENTS

| 4,880,005 A | 11/1989 | Pless et al. |
| 5,201,321 A | 4/1993 | Fulton |
| 5,439,004 A | 8/1995 | Duong-Van et al. |
| 5,712,801 A | 1/1998 | Turcott |
| 5,730,142 A | 3/1998 | Sun et al. |
| 6,487,443 B2 | 11/2002 | Olson et al. |
| 6,490,479 B2 * | 12/2002 | Bock .............................. 600/518 |
| 6,731,978 B2 | 5/2004 | Olson et al. |
| 6,871,089 B2 | 3/2005 | Korzinov et al. |
| 6,889,080 B2 | 5/2005 | Henry et al. |
| 6,922,584 B2 | 7/2005 | Wang et al. |
| 6,937,887 B2 | 8/2005 | Bock |
| 7,031,765 B2 | 4/2006 | Ritscher et al. |
| 7,050,846 B2 * | 5/2006 | Sweeney et al. .............. 600/515 |
| 7,092,751 B2 | 8/2006 | Erkkila |
| 7,120,485 B2 | 10/2006 | Glass et al. |
| 7,146,206 B2 | 12/2006 | Glass et al. |
| 7,187,965 B2 | 3/2007 | Bischoff et al. |
| 7,194,300 B2 * | 3/2007 | Korzinov ....................... 600/518 |
| 7,212,850 B2 | 5/2007 | Prystowsky |
| 7,353,057 B2 | 4/2008 | Schiessle et al. |
| 2002/0138012 A1* | 9/2002 | Hodges et al. ................ 600/509 |

(Continued)

OTHER PUBLICATIONS

Arzbaecher, Robert et al., "Automatic Tachycardia Recognition," PACE. 1984;7(Pt. II):541-547.

(Continued)

Primary Examiner — George Evanisko
Assistant Examiner — Lindsey G Hankins

(57) ABSTRACT

Detection of atrial fibrillation involves detecting a plurality of ventricular events and obtaining a series of probabilities of AF, each corresponding to a probability of AF for a different beat window having a plurality of ventricular events. AF onset is detected when one or each of a plurality of consecutive AF probabilities satisfies an AF trigger threshold. AF termination is detected when one or each of a plurality of consecutive AF probabilities does not satisfy the AF trigger threshold. A probability of AF is obtained using one or more of a probability of AF that is based on the presence of irregularity of the ventricular events ($P_{MC}$); a probability of AF that is based on variances of R-R intervals of the ventricular events ($P_{VAR}$); and/or a combination of these probabilities ($P_{COMBINED}$).

10 Claims, 15 Drawing Sheets

U.S. PATENT DOCUMENTS

| | | | |
|---|---|---|---|
| 2004/0230109 | A1 | 11/2004 | Schiessle et al. |
| 2005/0234313 | A1* | 10/2005 | Rowlandson et al. ........ 600/301 |
| 2006/0084883 | A1 | 4/2006 | Linker |
| 2006/0167364 | A1 | 7/2006 | Houben |
| 2006/0200036 | A1* | 9/2006 | Kurzweil et al. ............. 600/518 |
| 2006/0247547 | A1 | 11/2006 | Sarkar et al. |
| 2006/0247548 | A1 | 11/2006 | Sarkar et al. |
| 2006/0276716 | A1 | 12/2006 | Healey et al. |
| 2007/0073177 | A1 | 3/2007 | Kontothanassis et al. |
| 2007/0100248 | A1 | 5/2007 | Van Dam et al. |
| 2008/0161703 | A1 | 7/2008 | Houben et al. |

OTHER PUBLICATIONS

Moody, George B. et al. (Massachusetts Institute of Technology, Cambridge, MA; and Beth Israel Hospital, Boston, MA), "A New Method for Detecting Atrial Fibrillation Using R-R Intervals," IEEE—Computers in Cardiology. 1983:227-230.

Young, Brian et al. (GE Marquette Medical Systems, Milwaukee, WI), "A Comparative Study of a Hidden Markov Model Detector for Atrial Fibrillation," IEEE. 1999:468-476.

NonFinal Office Action, mailed May 25, 2011—Related U.S. Appl. No. 12/207,388.

* cited by examiner

| ALL VAR | +VAR | −VAR | $P_{VAR}$ |
|---------|------|------|-----------|
| 0 | 0 | 0 | 4 |
| . | . | . | . |
| . | . | . | . |
| . | . | . | . |
| 8 | 8 | 8 | 85 |
| . | . | . | . |
| . | . | . | . |
| . | . | . | . |
| 15 | 15 | 15 | 85 |

*FIG. 5B*

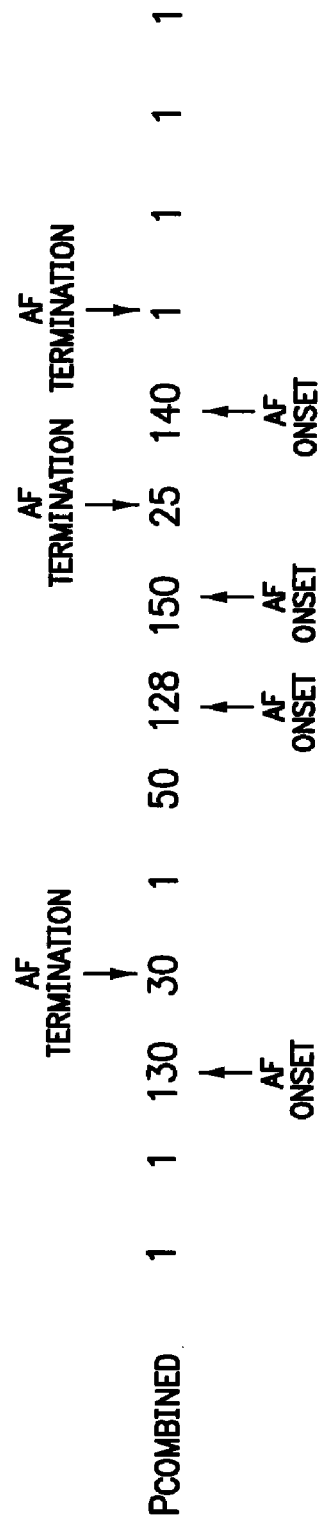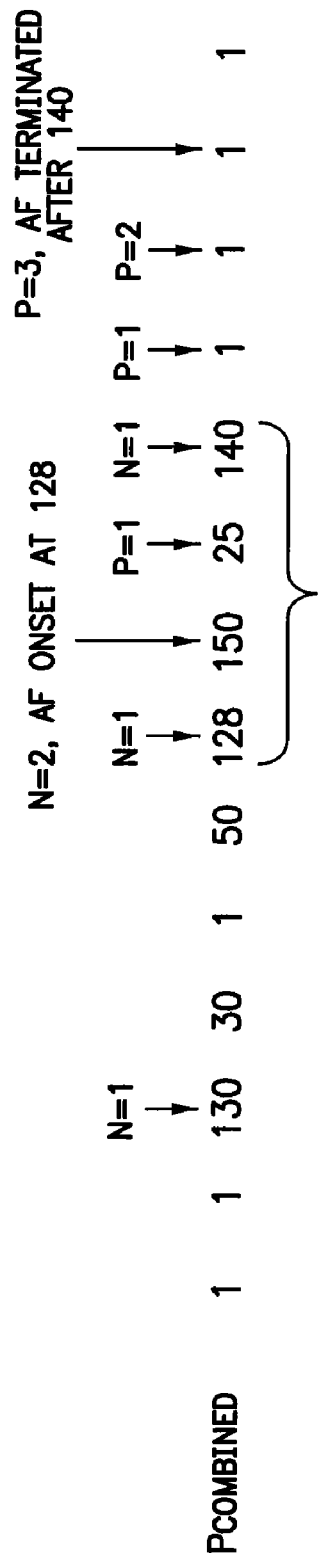

| TR | 0 | 1000 | 2000 | 3001 | 4001 | 5001 | 6003 | 7007 | 8009 | 9009 | 10009 |
|---|---|---|---|---|---|---|---|---|---|---|---|
| RR | 1000 – 0 = 1000 | 2000 – 1000 = 1000 | 3001 – 2000 = 1001 | 4001 – 3001 = 1000 | 5001 – 4001 = 1000 | 6003 – 5001 = 1002 | 7007 – 6003 = 1004 | 8009 – 7007 = 1002 | 9009 – 8009 = 1000 | 10009 – 9009 = 1000 | |
| dRR | 1000 – 1000 = 0 | 1001 – 1000 = 1 | 1000 – 1001 = –1 | 1000 – 1000 = 0 | 1002 – 1000 = 2 | 1004 – 1002 = 2 | 1002 – 1004 = –2 | 1000 – 1002 = –2 | 1000 – 1000 = 0 | | |

FIG. 10

| dRR | 0 | 1 | –1 | 0 | 2 | 2 | –2 | –2 | 0 |
|---|---|---|---|---|---|---|---|---|---|
| BIN | –2<0<=0 1 | 0<0<=1 2 | 2<–1<=0 1 | 2<0<=0 1 | 1<2 3 | 1<2 3 | –2<=–2 0 | –2<=–2 0 | –2<0<=0 1 |

| OFFSET | 1 | 2 | 1 | 1 | 3 | 3 | 0 | 1 |
|---|---|---|---|---|---|---|---|---|
| | 1*4+2 = 6 | 2*4+1 = 11 | | | | | | |
| | | | 1*4+1 = 5 | | | | | |
| | | | | 1*4+3 = 7 | | | | |
| | | | | | 3*4+3 = 15 | | | |
| | | | | | | 3*4+0 = 12 | | |
| | | | | | | | 0*4+0 = 0 | |
| | | | | | | | | 0*4+1 = 1 |

BIN

| 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 0 | 0 | 0 | 0 | 0 | 1 | 1 | 1 | 0 | 0 | 0 | 1 | 0 | 0 | 0 | 0 |

| 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 0% | 0% | 0% | 0% | 0% | 25% | 25% | 25% | 0% | 0% | 0% | 25% | 0% | 0% | 0% | 0% |

NON AF (162):

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| NON AF | 0% | 0% | 0% | 0% | 0% | 0% | 0% | 0% | 0% | 0% | 100% | 0% | 0% | 0% | 0% | 0% |

AF (160):

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| AF | 6% | 6% | 7% | 6% | 6% | 7% | 6% | 6% | 7% | 6% | 5% | 6% | 7% | 6% | 6% | 7% |

FIG. 16

Table 140:

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| SAMPLE CHAIN | 0% | 0% | 0% | 0% | 0% | 25% | 25% | 25% | 0% | 0% | 0% | 25% | 0% | 0% | 0% | 0% |
| NON AF CHAIN | 0% | 0% | 0% | 0% | 0% | 0% | 0% | 0% | 0% | 0% | 100% | 0% | 0% | 0% | 0% | 0% |
| DISTANCE | $(0-0)^2=0$ | $(0-0)^2=0$ | $(0-0)^2=0$ | $(0-0)^2=0$ | $(0-0)^2=0$ | $(25-0)^2=625$ | $(25-0)^2=625$ | $(25-0)^2=625$ | $(0-0)^2=0$ | $(0-0)^2=0$ | $(100-0)^2=10000$ | $(25-0)^2=625$ | $(0-0)^2=0$ | $(0-0)^2=0$ | $(0-0)^2=0$ | $(0-0)^2=0$ |

Table 142:

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| SAMPLE CHAIN | 0% | 0% | 0% | 0% | 0% | 25% | 25% | 25% | 0% | 0% | 0% | 25% | 0% | 0% | 0% | 0% |
| AF CHAIN | 6% | 6% | 7% | 6% | 6% | 7% | 6% | 6% | 7% | 6% | 5% | 6% | 7% | 6% | 6% | 7% |
| DISTANCE | $(0-6)^2=36$ | $(0-6)^2=36$ | $(0-7)^2=49$ | $(0-6)^2=36$ | $(0-6)^2=36$ | $(25-7)^2=324$ | $(25-6)^2=362$ | $(25-6)^2=362$ | $(0-7)^2=49$ | $(0-6)^2=36$ | $(0-5)^2=25$ | $(25-6)^2=362$ | $(0-7)^2=49$ | $(0-6)^2=36$ | $(0-6)^2=36$ | $(0-7)^2=49$ |

OLD CHAIN (6, 11, 5, 7)

| 0 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| 0% | 0% | 0% | 0% | 0% | 25% | 25% | 25% | 0% | 0% | 0% | 25% | 0% | 0% | 0% | 0% |

NEW CHAIN (11, 5, 7, 15)

| 0 | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| 0% | 0% | 0% | 0% | 0% | 25% | 0% | 25% | 0% | 0% | 0% | 25% | 0% | 0% | 0% | 25% |

FIG. 18

DEVICE AND METHOD FOR DETECTING ATRIAL FIBRILLATION

CROSS REFERENCE TO RELATED APPLICATIONS

This application claims the benefit of U.S. Provisional Patent Application Ser. No. 61/048,129, filed Apr. 25, 2008, titled "Device and Method for Detecting Atrial Fibrillation," and is related to copending U.S. patent application Ser. No. 12/207,388, filed Sep. 9, 2008, titled "Device and Method for Detecting Atrial Fibrillation".

FIELD OF THE INVENTION

The invention relates generally to the monitoring of heart rate variability, and more particularly to devices and methods for detecting atrial fibrillation.

BACKGROUND

Atrial fibrillation is a common and serious cardiac arrhythmia, affecting more than two million people in the United States alone. Clinically, atrial fibrillation involves an abnormality of electrical impulse formation and conduction that originates in the atria. Atrial fibrillation is characterized by multiple swirling wavelets of electrical current spreading across the atria in a disorganized manner. The irregularity of electrical conduction throughout the atria creates irregular impulse propagation through the atrioventricular (AV) node into the ventricle.

Impulse propagation through the AV node may be extremely rapid, leading to reduced diastolic filling of the heart chambers and a corresponding reduction of the cardiac pumping action. Increased heart rate and loss of AV synchrony may also exacerbate any underlying heart problems, such as heart failure, coronary blood flow, or other pulmonary disorders.

Alternatively, impulse propagation through the AV node may be very limited due to AV node refractoriness so that atrial fibrillation can be sustained indefinitely, since the ventricles continue to drive circulation, albeit inefficiently. The risks of sustained atrial fibrillation are nevertheless serious including stroke and myocardial infarctions caused by the formation of blood clots within stagnant volumes in the atria.

Often the symptoms of atrial fibrillation (AF) occur infrequently so that AF can only be detected by continuous cardiac electrical activity monitoring over a long period of time on an ambulatory subject. AF monitoring systems for use in an ambulatory setting may be either external, such as a Holter monitor, or internal. These systems continually sense cardiac electrical signals from a patient's heart, process the signals to detect AF and upon detection, record the electrical signals for subsequent review and analysis by a care provider.

SUMMARY

Briefly, and in general terms, the invention relates to devices and methods for detecting atrial fibrillation. In one aspect, the invention relates to a cardiac rhythm monitoring device that includes electrodes that are adapted to be coupled to a patient to sense cardiac electrical activity. A processor is coupled to the electrodes to receive the electrical activity and is programmed to detect ventricular events within the electrical activity. The processor is also programmed to—for a first beat window of a plurality of detected ventricular events—determine a probability of AF based on the presence of irregularity of the ventricular events; determine a probability of AF based on variances of R-R intervals of the ventricular events; and combine the probabilities to obtain a first-beat-window combined probability of AF.

In another aspect, the invention relates to a method of detecting atrial fibrillation that includes detecting a plurality of ventricular events; determining a probability of AF for each of a plurality of beat windows, each beat window having a plurality of ventricular events, to obtain a series of probabilities; and detecting AF onset when each of a plurality of consecutive AF probabilities satisfies an AF trigger threshold and AF termination when each of a plurality of consecutive AF probabilities does not satisfy the AF trigger threshold.

These and other aspects of the invention will become apparent from the following detailed description and the accompanying drawings which illustrate by way of example the features of the invention.

BRIEF DESCRIPTION OF THE DRAWINGS

FIG. 5B is an illustration of a look-up table relating three different variance calculation and corresponding variance probability ($P_{VAR}$) values;

FIG. 7 is an exemplary series of combined probabilities ($P_{COMBINED}$) evaluated in accordance with the technique of FIG. 6A to determine corresponding AF onset and AF termination beats;

FIG. 8 is an exemplary series of combined probabilities ($P_{COMBINED}$) evaluated in accordance with a technique involving hysteresis;

FIG. 10 is an illustration of an eleven beat window and corresponding RR interval and dRR values;

FIG. 11 is an illustration of the dRR values of FIG. 10 and their corresponding BIN values;

FIG. 12 is an illustration of the BIN values of FIG. 11 and their corresponding offset values;

FIG. 13 is an illustration of a sample statistic chain, in count terms, derived from the first four offset values of FIG. 12;

FIG. 14 is an illustration of a sample statistic chain, in percentage terms, derived from the first four offset values of FIG. 12;

FIG. 15 is an illustration of a non AF statistic chain and an AF statistic chain, both in percentage terms;

FIG. 16 is an illustration of distance comparisons between the sample statistic chain of FIG. 14 and the non AF and AF statistic chains of FIG. 15;

FIG. 18 is an illustration of the sample statistic chain of FIG. 14 and a new sample statistic chain derived from the second through fifth offset values of FIG. 12.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

Overview of Implantable Monitoring Device

Figure 1:
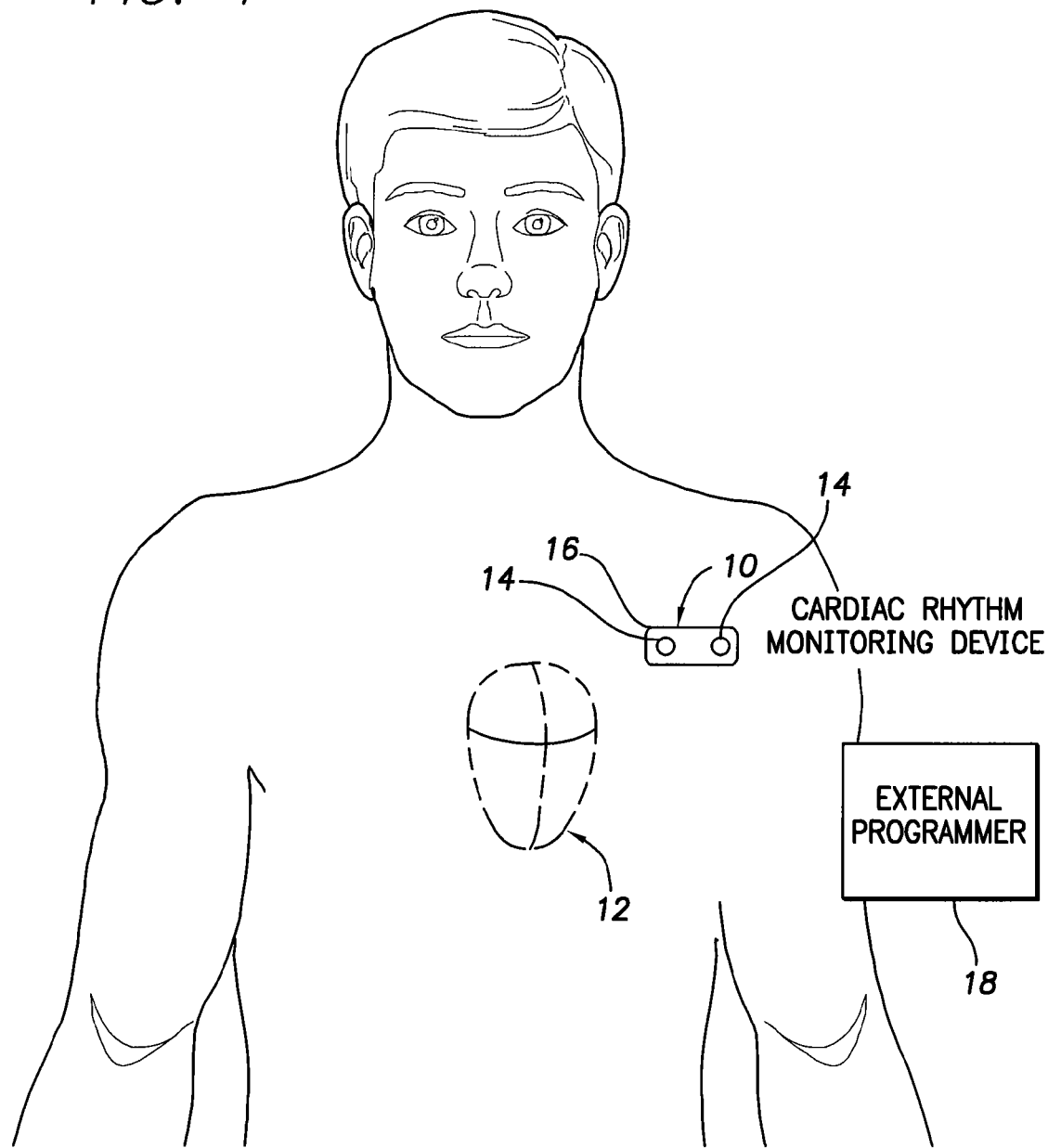
FIG. 1 illustrates pertinent components of a cardiac rhythm monitoring system capable of monitoring heart rate variability and detecting atrial fibrillation (AF)

Referring now to the drawings and particularly to FIG. 1, there is shown an implantable monitoring device 10 intended for subcutaneous implantation at a site near the heart 12. The monitoring device includes a pair of spaced-apart sense electrodes 14 positioned with respect to a housing 16. The sense electrodes 14 provide for detection of far field electrogram signals. Numerous configurations of electrode arrangements are possible. For example, the electrodes 14 may be located on the same side of the housing 16. Alternatively, the electrodes 14 may be located on opposite sides of the housing 16. One of the electrodes 14 may be formed as part of the housing 16, for example, by coating all but a portion of the housing with a nonconductive material such that the uncoated portion forms the electrode. In this case, the other of the electrodes 14 may be electrically isolated from the housing electrode by placing it on a component separate from the housing, such as a header (not shown). In other configurations, the electrodes 14 may be located on short, stub leads extending away from the housing but coupled thereto through one or more headers so as to interface with internal components. The housing 16 includes various other components such as: sense electronics for receiving signals from the electrodes, a microprocessor for processing the signals in accordance with algorithms, such as the AF detection algorithm described herein, a loop memory for temporary storage of electrograms, a device memory for long-term storage of electrograms upon certain triggering events, such as AF detection, sensors for detecting patient activity and a battery for powering components.

The monitoring device 10 senses far field electrograms; processes the electrograms to detect arrhythmias and if an arrhythmia is detected; automatically records the electrograms in memory for subsequent transmission to an external device 18. Electrogram processing and arrhythmia detection is provided for, at least in part, by algorithms embodied in the microprocessor. In one configuration, the monitoring device is operative to detect atrial fibrillation.

Atrial Fibrillation (AF) Detection Algorithm Overview

Figure 2:
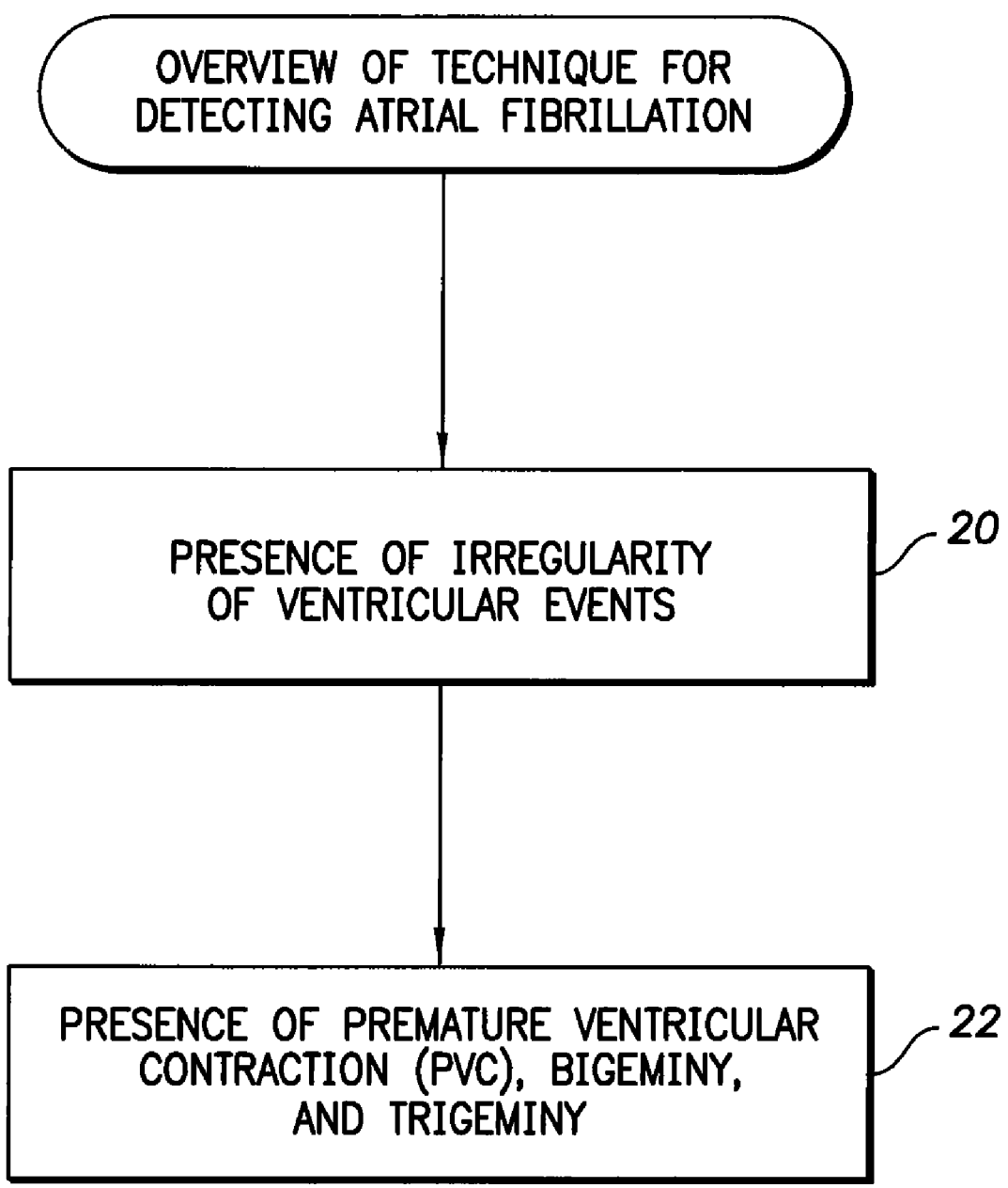
FIG. 2 is an overview flow chart of a technique for detecting AF.

With reference to FIG. 2, an AF detection algorithm in accordance with the invention, detects episodes of AF by evaluating ventricular responses to atrial events during AF. The ventricular response criteria evaluated in this algorithm include one or more of the following:

1. Presence of irregularity of ventricular events, i.e., R waves (block 20).
2. Presence of premature ventricular contraction (PVC), bigeminy, and trigeminy based on statistical analysis on R wave interval features (block 22).

The two criteria 20, 22 are used to compute the probability that a current heart beat is AF. If the probability satisfies a threshold criteria, AF is considered "detected" or "onset" for the current beat. More detailed description of the implementation and interaction between the above two criteria follows.

Detecting the Presence of Irregularity of Ventricular Events: Obtaining Markov-Chain Based Probability ($P_{MC}$)

This portion of the AF detection algorithm determines the probability of a current beat to be AF based on the interval stability of a previous number of beats (including the current beat), herein referred to as a "beat window" or "epoch." In one configuration, the number of beats within a beat window is 64.

Figure 3:
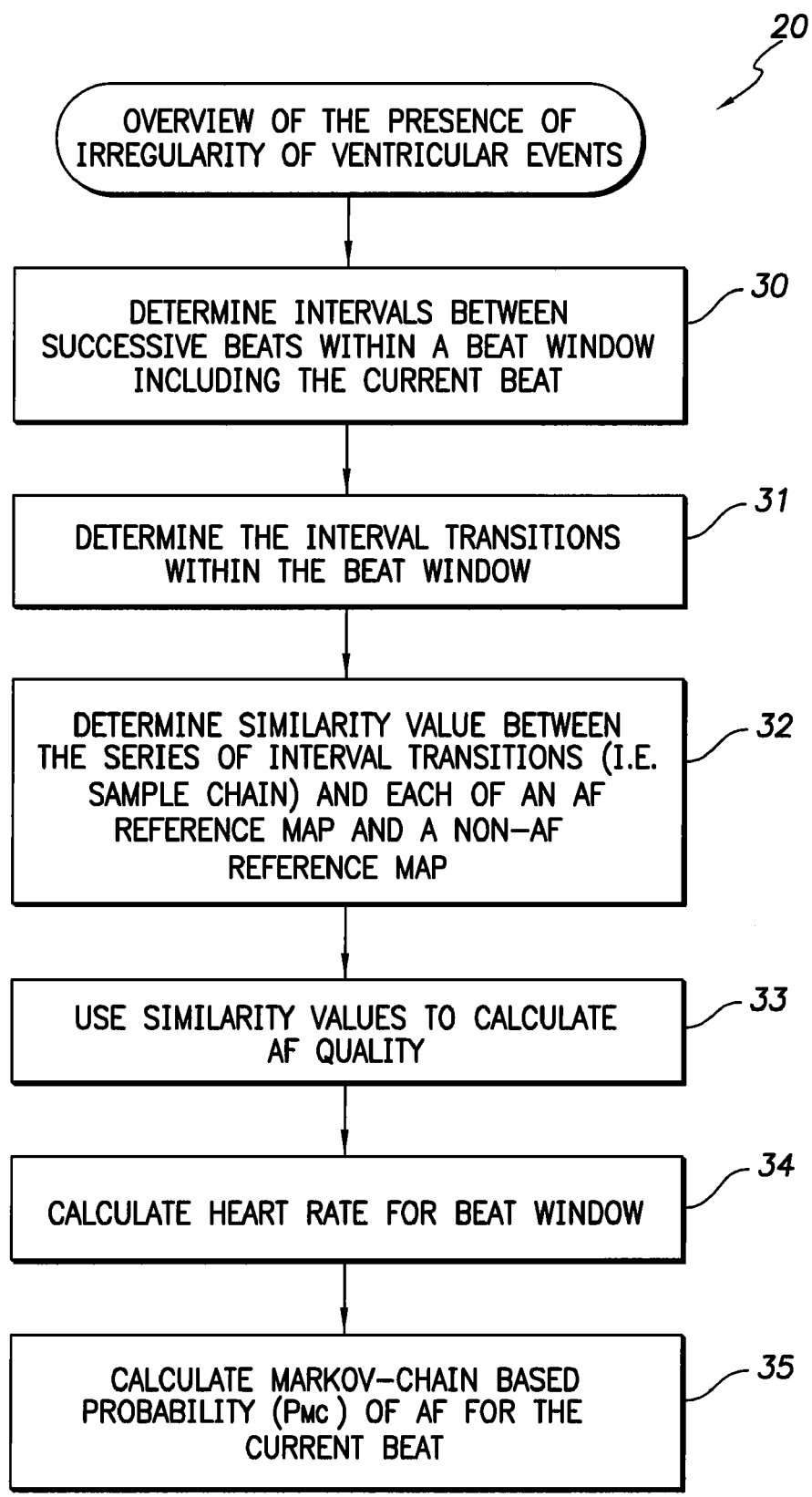
FIG. 3 is an overview flow chart of one aspect of the technique of FIG. 2 related to the presence of irregularity of ventricular events and involves AF quality, heart rate and Markov-Chain probability ($P_{MC}$) calculation.

With reference to FIG. 3, at block 30 the algorithm determines the intervals between successive beats within a beat window. At block 31 the transitory behavior of one interval to another is assessed using a Markov-Chain model that involves determining interval transitions within the beat window. Prior work in AF detection utilizing a Markov-Chain based model is described by Moody et al. in "A New Method for Detecting Atrial Fibrillation Using R-R Interval," Computers in Cardiology 1983, the disclosure of which is hereby incorporated by reference and Young et al. in "A Comparative Study of a Hidden Markov Model Detection for Atrial Fibrillation," IEEE 1999, pages 468-476.

At block 32, the series of interval transitions within the beat window, also referred to as the "sample chain" or "sample statistics chain" is compared to known interval state transitions during AF, referred to herein as an AF reference map (or alternatively as an "AF chain" or "AF statistic chain"), and to known interval transitions during non-AF, referred to herein as a non-AF reference map (or alternatively as a "non-AF chain" or "non-AF statistic chain") to determine a similarity value between the sample chain and the reference maps. In one configuration, the similarity value is determined by calculating the Euclidian distance between the sample chain and each of the AF reference map and the non-AF reference map. In one embodiment, the comparisons between the interval transitions within the beat window and the AF reference map and the non-AF reference map are performed in manners similar to those disclosed in U.S. Pat. No. 5,712,801 by Robert Turcott titled "Method of Characterizing Dynamical Systems," the disclosure of which is hereby incorporated by reference.

At block 33, the algorithm uses the similarity values in the form of Euclidian distance to determine AF quality using the following equation:

$$AF\ Quality = \frac{\text{Euclidian distance to non } AF \text{ reference map}}{\text{Euclidian distance to } AF \text{ reference map}} \quad \text{(Eq. 1)}$$

At block 34, a heart rate is calculated for the beat window, using all or just a portion of the beats within the window. As explained further below (e.g., Eq. 7) the heart rate is calculated in terms of a heart rate index. At block 35 the AF quality and heart rate (HR) index for the beat epoch are used as inputs to search for a Markov-Chain based probability ($P_{MC}$) of AF from a probability look-up table. The probability look-up table for $P_{MC}$ is created from AF quality versus heart rate distributions for the known AF beats and known non-AF beats from well-known public databases, including the MIT-BIH Atrial Fibrillation database, the American Heart Association (AHA) database, European ST-T database, and AF Termination Challenge database, all available at physionet.org and AHA. AF Quality and heart rate index are calculated for each of known AF data and known non AF data within these databases using the same processes and equations (e.g., Eq. 1 and Eq. 7) described herein. A graphical presentation of a possible look-up table of heart rate index verses AF Quality verses $P_{MC}$ is provided in FIG. 4. With regard to FIG. 4, it is noted that a higher heart rate index corresponds to a lower heart rate.

Detecting the Presence of PVC, Bigeminy, and Trigeminy: Obtaining Variance Probability ($P_{VAR}$)

$P_{MC}$ alone, as computed above, may be indiscriminate in distinguishing RR interval instability due to AF from RR interval instability due to PVCs, bigeminy, and trigeminy. Accordingly, this feature of the algorithm is intended to prevent false detection of AF by discriminating AF beats against beats from premature ventricular contractions (PVC), bigeminy, and trigeminy. By way of background, bigeminy is a cardiac rhythm characterized by pairs of complexes. This commonly refers to a ventricular ectopic beat coupled to a sinus beat, but it could also be an atrial ectopic beat or paced ventricular beat coupled to either a conducted ventricular complex or a ventricular ectopic beat. Trigeminy is an arrhythmia characterized by repeating patterns of three beats, with one premature ventricular contraction following two normal beats.

Figure 5A:
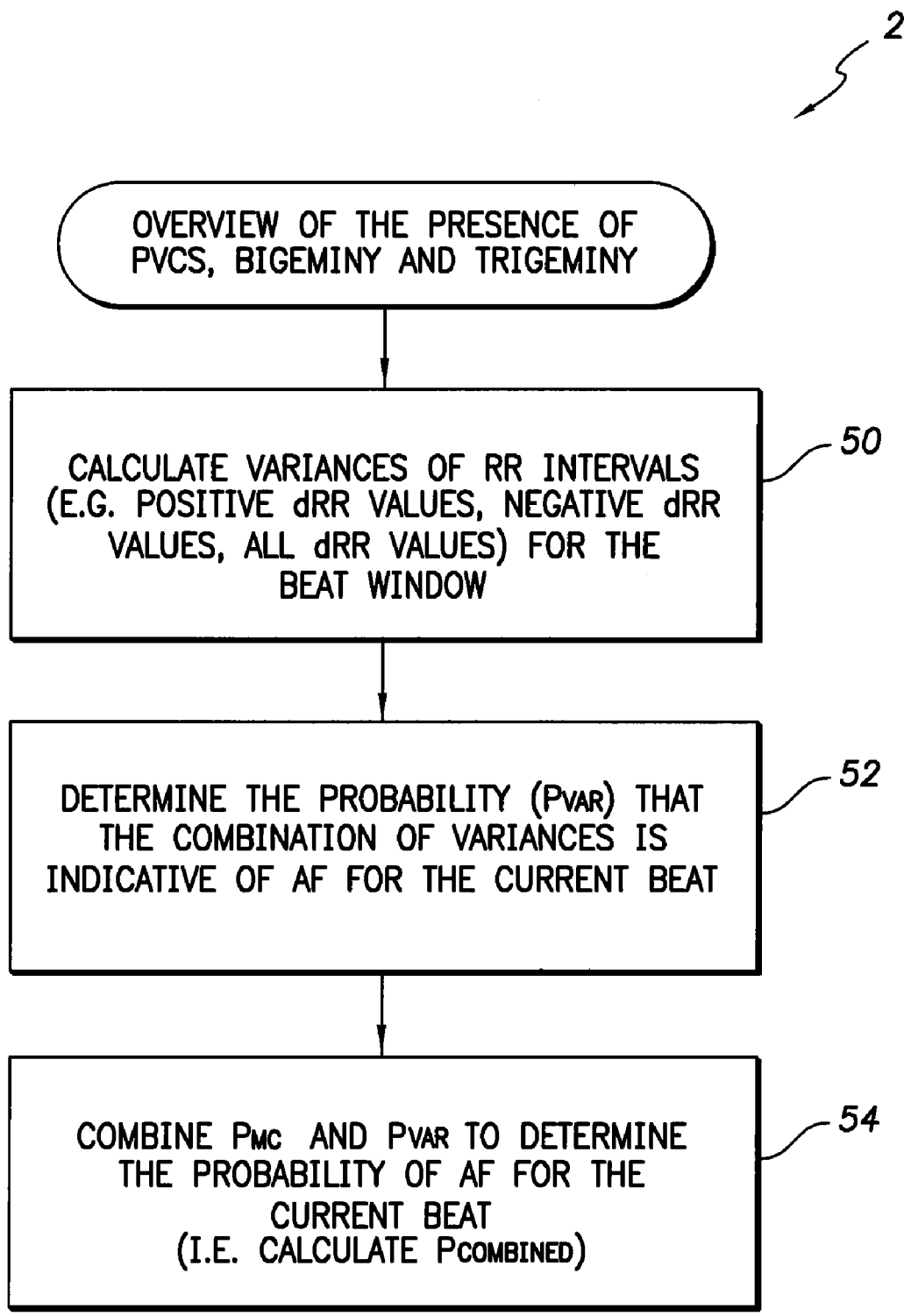
FIG. 5A is an overview flow chart of one aspect of the technique of FIG. 2 related to the presence of premature ventricular contractions (PVCs), bigeminy and trigeminy and involves variance probability ($P_{VAR}$) and combined probability ($P_{COMBINED}$) calculations.

With reference to FIG. 5A, in block 50, variances may be calculated based on a predetermined number of RR intervals within the same beat window used to determine $P_{MC}$. For computational efficiency, this predetermined number is typically a subset of the total number in the beat window. In one configuration, the following three types of variances are computed.

1. Variance based on positive values of dRR (+Var)
2. Variance based on negative values of dRR (−Var)
3. Variance based on all values dRR (all Var)

Figure 5B:
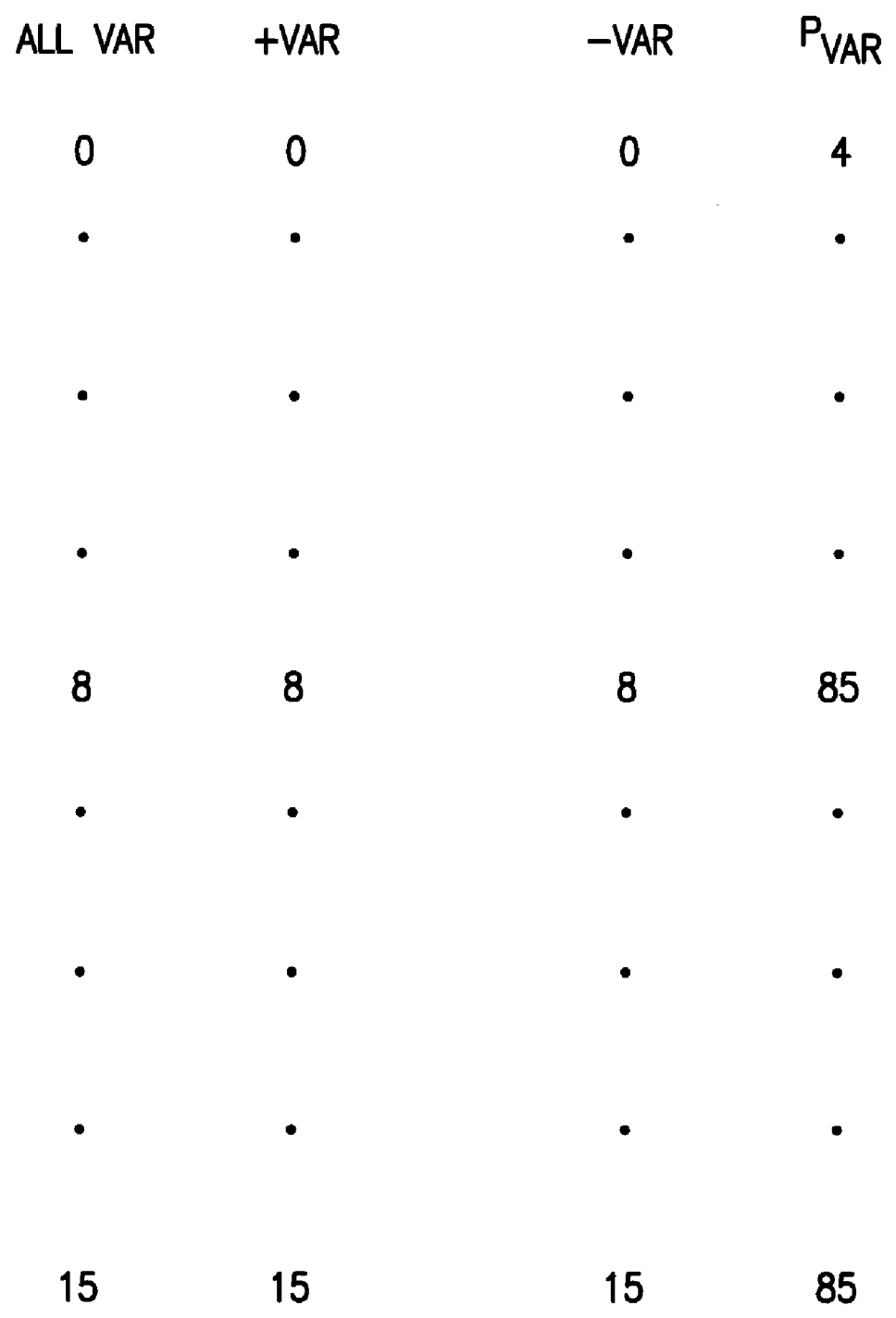

At block 52, the three types of variances of unknown beats are used as input to search for variance based probability ($P_{VAR}$) of a beat being AF instead of a beat of other ectopic origins, e.g., PVCs, bigeminy, and trigeminy, from a probability look-up table. Variances are calculated for each of known AF data vs. PVCs, bigeminy, and trigeminy data within the databases referenced above. An exemplary look-up table of variance inputs verses $P_{VAR}$ is provided in FIG. 5B.

At block 54, the Markov-Chain based probability of AF ($P_{MC}$) and the variance-based probability of AF ($P_{VAR}$) are combined to determine the probability of AF for the current beat (i.e., combined probability $P_{COMBINED}$). In the case where $P_{COMBINED}$ is being determined for the first time, the following equation is used:

$$P_{COMBINED} = \frac{P_{MC} * P_{VAR}}{P_{MC} * P_{VAR} + (1 - P_{MC}) * (1 - P_{VAR})} \quad \text{(Eq. 2)}$$

In cases where $P_{COMBINED}$ has been determined for a previous beat window, $P_{COMBINED}$ for the current beat window is determined by combining the Markov-Chain based probability of AF ($P_{MC}$) of the current window and the variance-based probability of AF ($P_{VAR}$) of the current window with $P_{COMBINED}$ for the previous window, using the following equation:

$$P_{COMBINED} = \frac{P_{VAR} * P_{COMBINEDx}}{P_{VAR} * P_{COMBINEDx} + (1 - P_{VAR}) * (1 - P_{COMBINEDx})} \quad \text{(Eq. 3)}$$

where:

$$P_{COMBINEDx} = \frac{P_{MC} * P_{COMBINED\ previous}}{P_{MC} * P_{COMBINED\ previous} + (1 - P_{MC}) * (1 - P_{COMBINED\ previous})}$$

As described further below with reference to FIGS. 6A and 6B, once $P_{COMBINED}$ is determined, it is compared to an AF trigger threshold. If $P_{COMBINED}$ satisfies the threshold AF onset is considered to be detected. It is also possible that only one of the two probabilities ($P_{MC}$ and $P_{VAR}$) calculated for the given epoch is used with or without $P_{COMBINED}$ previous to compute current $P_{COMBINED}$.

AF Onset and Termination

Figure 6A:
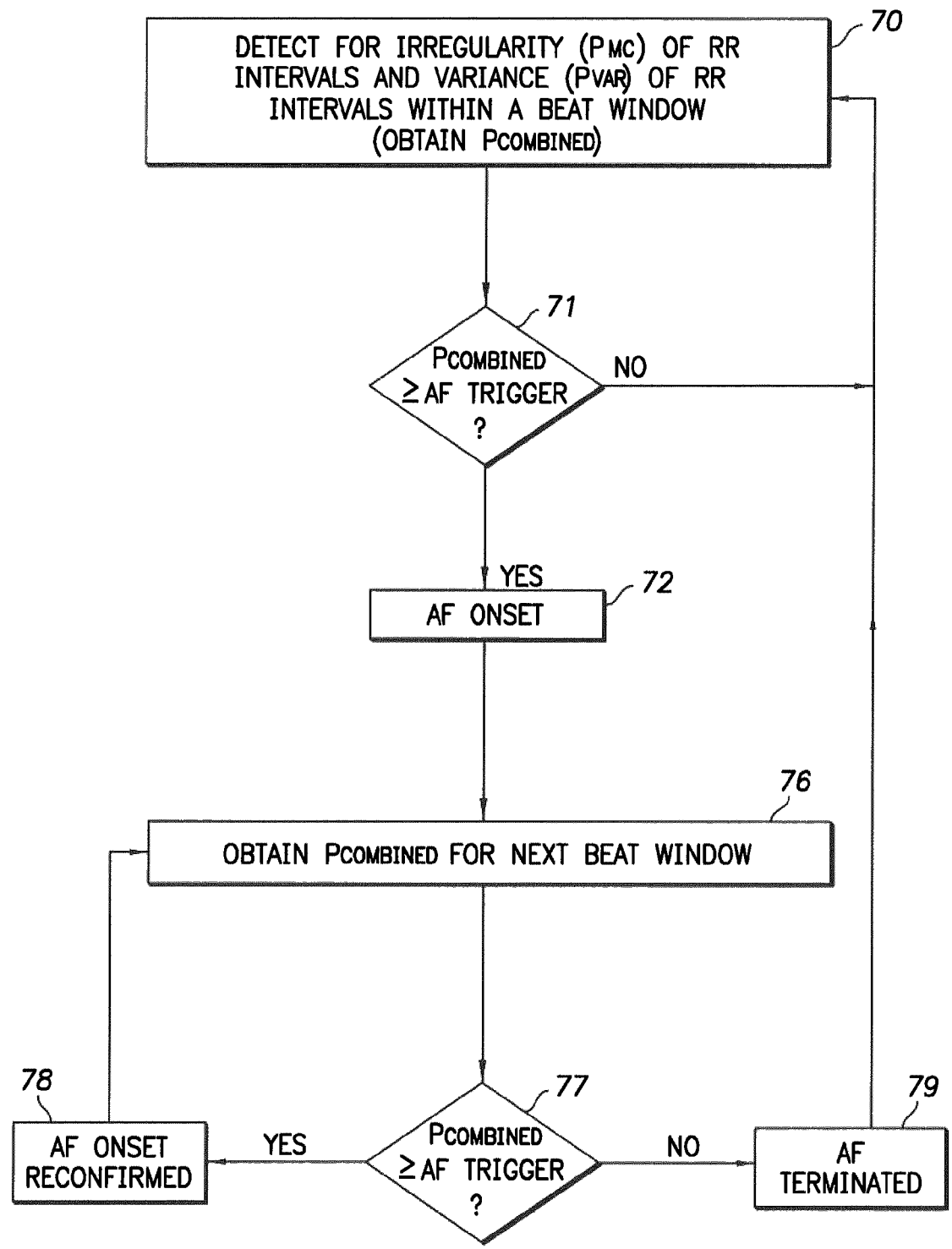
FIG. 6A is a flow chart illustrating a technique for detecting AF onset and AF termination.
Figure 6B:
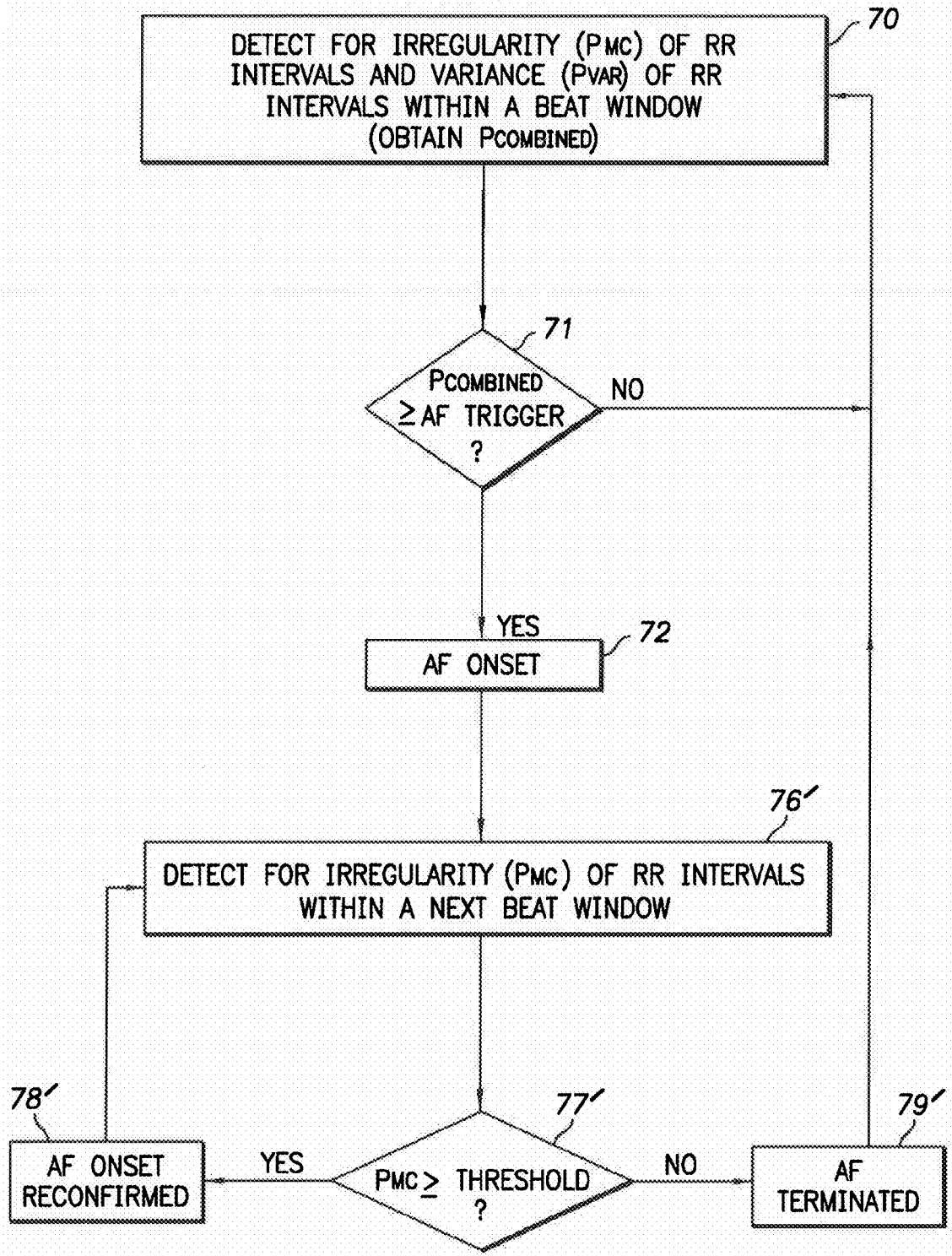
FIG. 6B is a flow chart illustrating an alternate technique for detecting AF onset and AF termination.

With reference to FIGS. 6A and 6B, the algorithm operates on a series of beat windows, each including a series of beats, to determine onset and termination of AF. To this end and with reference to FIG. 6A, in one configuration, at block 70, the algorithm detects for irregularity ($P_{MC}$) of RR intervals and variances ($P_{VAR}$) of RR intervals within a beat window, as described above with reference to FIGS. 3 and 5, to obtain a probability of AF, i.e., $P_{COMBINED}$. At block 71, $P_{COMBINED}$ is compared to an AF trigger threshold which is a programmable value that is typically at the center of the range of possible $P_{COMBINED}$ values. For example, if $P_{COMBINED}$ may range from 1 to 256, a center AF trigger threshold would be 128. However, AF trigger threshold could be set at other values to improve sensitivity and specificity.

If $P_{COMBINED}$ does not satisfy the AF trigger threshold, the process returns to block 70 where $P_{COMBINED}$ is determined for the next beat window. If $P_{COMBINED}$ does satisfy the AF trigger threshold, then AF onset is detected at block 72.

At block 76, the algorithm proceeds to the next beat window and determines $P_{COMBINED}$. At block 77, $P_{COMBINED}$ for the next beat window is compared to the AF trigger threshold. If $P_{COMBINED}$ for the next beat window satisfies the AF trigger threshold, AF onset is reconfirmed at block 78 and the process returns to block 77. If $P_{COMBINED}$ for the next beat window does not satisfy the AF trigger threshold, then the algorithm determines that AF has terminated at block 79 and returns to block 70 to start the process over with the next beat window.

With reference to FIG. 6B, in an alternate configuration, only irregularity of RR intervals, i.e., the Markov-Chain based probability of AF, $P_{MC}$ with or without $P_{COMBINED}$ previous, is used to reconfirm or terminate AF. In some instances this may be preferential to using $P_{COMBINED}$ because $P_{COMBINED}$ may tend to present false positive AF terminations, thus leading to fragmented periods of AF detection, e.g., frequent toggling between AF onset and AF termination, whereas false positive AF terminations is not as prevalent with $P_{MC}$. It is still possible that only $P_{VAR}$ with or without $P_{COMBINED}$ previous is used to detect the termination of AF.

In the process of FIG. 6B, blocks 70 through 72 are the same as described for FIG. 6A. The algorithm is different beginning at block 76' wherein it detects for irregularity ($P_{MC}$) of RR intervals in the next beat window, as opposed to $P_{COMBINED}$. At block 77', the algorithm compares $P_{MC}$ to a predetermined threshold. If $P_{MC}$ satisfies the threshold the algorithm reconfirms AF onset at block 78' and returns to block 76' where it detects for irregularity ($P_{MC}$) of RR intervals in the next beat window. If, however, $P_{MC}$ fails to satisfy the threshold, the algorithm determines that AF has terminated at block 79' and returns to block 70 to continue the process on the next beat window.

From the processes of FIGS. 6A and 6B, it is noted that with respect to initial AF onset, both $P_{MC}$ and $P_{VAR}$ are involved in the determination process. For the process of FIG. 6A, both $P_{MC}$ and $P_{VAR}$ are involved in the reconfirmation and termination processes, whereas for the process of FIG. 6B, termination of AF is made solely by the Markov-Chain based probability of AF, i.e., $P_{MC}$.

The algorithm may be considered to operate on a series of $P_{COMBINED}$ values, each corresponding to a respective beat window, to detect AF onset and termination. In its most simple form, AF is detected if the $P_{COMBINED}$ exceeds a trigger threshold and non AF is detected if $P_{COMBINED}$ is below a termination threshold For example, with reference to FIG. 7, if the $P_{COMBINED}$ series obtained by the process of FIG. 6A is: 1, 1, 130, 30, 1, 50, 128, 150, 25, 140, 1, 1, 1, 1, and the trigger threshold is 128, AF detection would trigger on at 130, 128, 150 and 140 and terminate for all other values.

More specifically, at 130 $P_{COMBINED}$ exceeds threshold 128 so there is AF onset (FIG. 6A, blocks 71 and 72). At 30, $P_{COMBINED}$ for the next beat window does not exceed the threshold 128 so AF is terminated (FIG. 6A, blocks 76, 77 and 79). At $P_{COMBINED}$=128, AF is onset again (FIG. 6A, blocks 70 through 72). At $P_{COMBINED}$=150, AF is reconfirmed (FIG. 6A, blocks 76, 77 and 78). At $P_{COMBINED}$=25, AF is terminated. At $P_{COMBINED}$=140, AF is onset again. At $P_{COMBINED}$=1, AF is terminated and is not onset for the remainder of the series of $P_{COMBINED}$ values.

In a more sophisticated arrangement, hysteresis is introduced in order to keep the number of switches between triggers and terminations to a minimum level. For example, to go from non AF to AF, the algorithm may require a series of N, $P_{COMBINED}$ values above or equal to a trigger threshold in a row. To go from AF to non AF, the algorithm may require a series of P, $P_{COMBINED}$ values below a termination threshold in a row.

With reference to FIG. 8, if the $P_{COMBINED}$ series is: 1, 1, 130, 30, 1, 50, 128, 150, 25, 140, 1, 1, 1, 1, the trigger threshold is 128 and the algorithm is set N=2 (two $P_{COMBINED}$ values above or equal to 128 are required to trigger AF onset), and P=3 (three $P_{COMBINED}$ values below 127 are required to terminate AF), then an AF section would correspond to the $P_{COMBINED}$ series: 128, 150, 25, 140.

Specifically, the algorithm does not trigger AF onset on the 130, as $P_{COMBINED}$ dropped to 30 immediately afterwards and thus N=2 was not satisfied. The algorithm does trigger AF onset at 128, once $P_{COMBINED}$ reached 150 because N=2 was satisfied at that point. The algorithm does not terminate AF at the 25 because it only had one level below the threshold and thus P=3 is not satisfied. While the algorithm did terminate AF after the 140, it does not make that distinction until it found the third 1 after the 140, thus satisfying P=3. These counts and thresholds are programmable. By adjusting them the algorithm can adjust the sensitivity/specificity to AF along with a tendency towards short or long durations.

ILLUSTRATIVE EMBODIMENT

Following is an illustrative example of the AF detection algorithm operating on an 11 beat epoch or beat window. Some abbreviations which are used throughout include:

$TR_N$ is the time of Nth R peak of the QRS complex. This number is found by a QRS detection hardware or software. It is a non-negative number.

$RR_N$ is the time between the Nth and Nth+1 R Peak. It is calculated by $TR_{N+1}-TR_N$. It is a non negative number.

$dRR_N$ is the time difference between the Nth and Nth+1 RR values. It is calculated by $RR_{N+1}-RR_N$. It can be negative, zero or a positive number.

Obtaining Markov-Chain Based Probability ($P_{MC}$)

Figure 9:
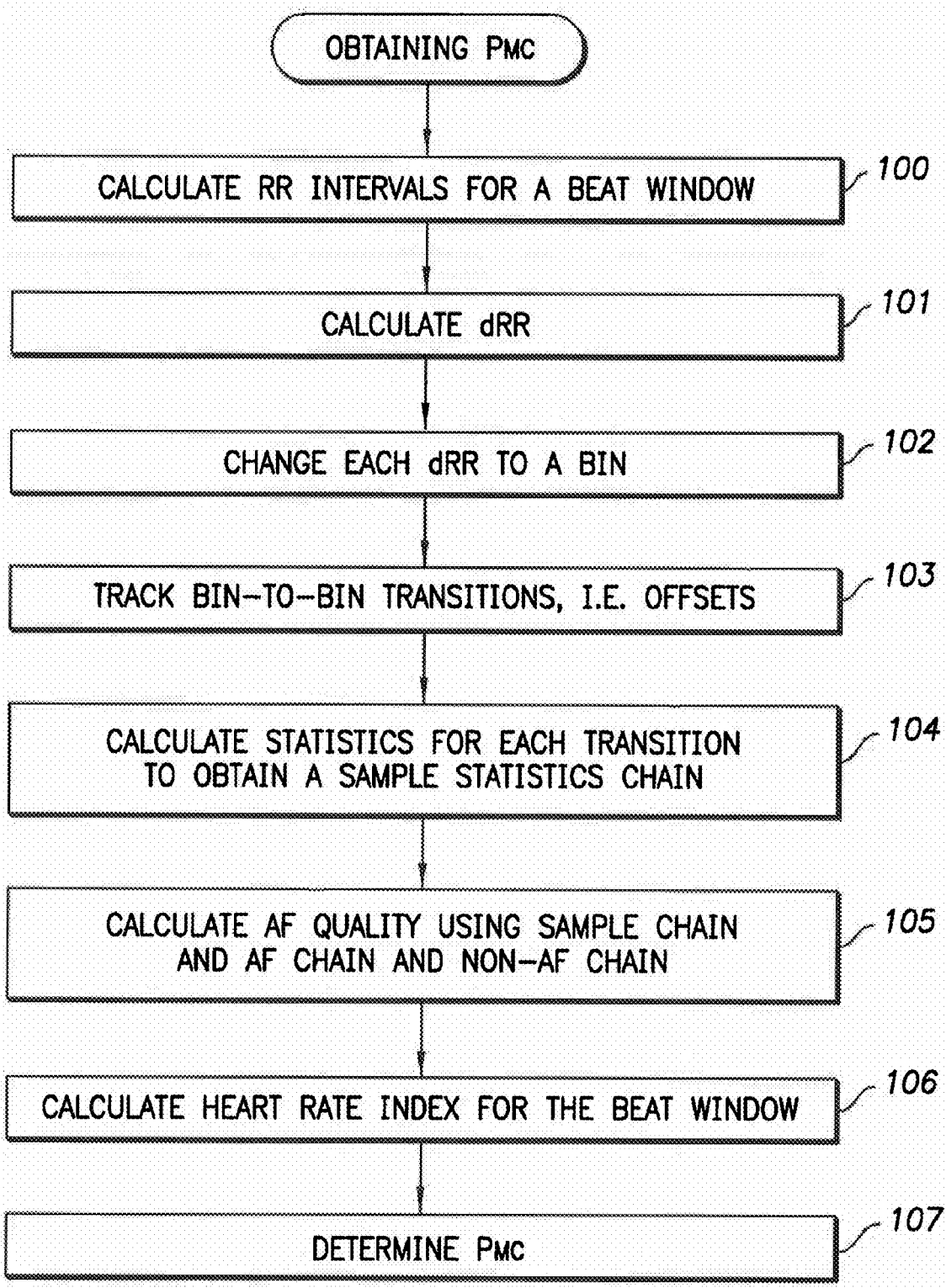
FIG. 9 is a flow chart illustrating a technique for obtaining Markov-Chain probability ($P_{MC}$) of AF.

With reference to FIG. 9, at block 100 RR intervals are calculated for each successive pair of adjacent R waves within a beat window based on the timing of the R waves. The result is a set of 10 RR intervals 110, as shown in FIG. 10. At block 101 the differences between successive RR intervals, i.e., dRRs, are calculated based on the RR intervals. The result is a set of 9 dRRs 112, as shown in FIG. 10.

At block 102, after the dRR values have been calculated the dRR values are changed into bins using some thresholds. This effectively changes the dRR values into a number of manageable states. This can be done with a series of "if" statements or a precomputed look up table for speed. While there can be a wide range of bins, e.g., 2 to 32, this example assumes there are 4 bins with the following corresponding thresholds:

if, dRR<=−2, then bin=0
if, −2<dRR=<0, then bin=1
if, 0<dRR=<1, then bin=2
if, dRR>1, then bin=3

With these thresholds, the dRR values 112 of FIG. 10 would then get changed into the bins 114 shown in FIG. 11. After a corresponding bin has been determined for each of the dRR values, at block 103, the algorithm keeps track of how bins transition from one bin to the next bin. Since in the example there are 4 bins, and each bin can transition to another bin including itself, for a single bin it is necessary to keep track of 4*4 bins, or 16 transition possibilities. To keep track of 2 transitions, there exists 4*4*4 bins or 64 transition possibilities. To generalize, if there are N states, and the goal is to keep track of P transitions, the end result is $N^{P+1}$ transition possibilities. For this example, the assumption is to only keep track of a single transition, which calculates to $4^2$ or 16 possible states.

With reference to FIG. 12, 8 transitions or "offsets" 116 are calculated for the 9 bins. The offset into one of 16 possible states can be calculated by taking the first bin and multiplying it by the size of that state and adding it to a second state. This is the same math that a compiler would do for a multidimensional array, but by computing it manually there is the possibility to avoid redundant calculations and gives the ability to change the dimensions whenever necessary. In this example, the offsets may be written as the list: 6, 11, 5, 7, 15, 12, 0, 1.

At block 104, in order to do an analysis over a given sample offset window size, statistics are calculated on each transition. This is done by first counting up the number of each offsets in a window, converting those counts into a percentage and then comparing it to another array or percentages of a known arrhythmia. This example assumes a sample offset window size of 4, but the window size could be anywhere from 1 to 100 beats. In this example, the first four offsets are: 6, 11, 5, 7. With reference to FIG. 13, by summing up each offset within the offset window, a count 118 of 1 can be put into the slots 120 of 6, 11, 5, and 7. With reference to FIG. 14, percentage wise, 25% of the offsets in the offset window are in the slots 6, 11, 5 and 7.

As mentioned above, the algorithm employs AF and non AF reference maps (or statistic chains) that are compared to the sample chain of statistics. An exemplary AF reference map 160 and non-AF reference map 162 are shown in FIG. 15. These maps may be obtained by subjecting known AF data and known non AF data to the processes of FIG. 9, blocks 100 through 104.

Continuing with FIG. 9, at block 105, AF Quality is calculated using the sample chain, AF chain and non AF chain. First, as described above, a simple Euclidian distance algorithm is used to calculate a "distance" from the sample statistic chain to the AF statistic chain and from the sample chain to the Non AF statistic chain. As shown in FIG. 16, this distance is the sum of the square of the differences. The distance of the non AF chain 140 is 12500 while the distance of the AF chain 142 is 1880. Next, the distances are used to AF quality as follows:

$$AF\ Quality = \frac{(non\ AF\ chain\ distance + 1)}{(AF\ chain\ distance + 1)} \quad \text{(Eq. 4)}$$

where: non AF chain distance=the Euclidian distance between the sample chain and the non AF chain; and AF chain distance=the Euclidian distance between the sample chain and the AF chain.

Figure 4:
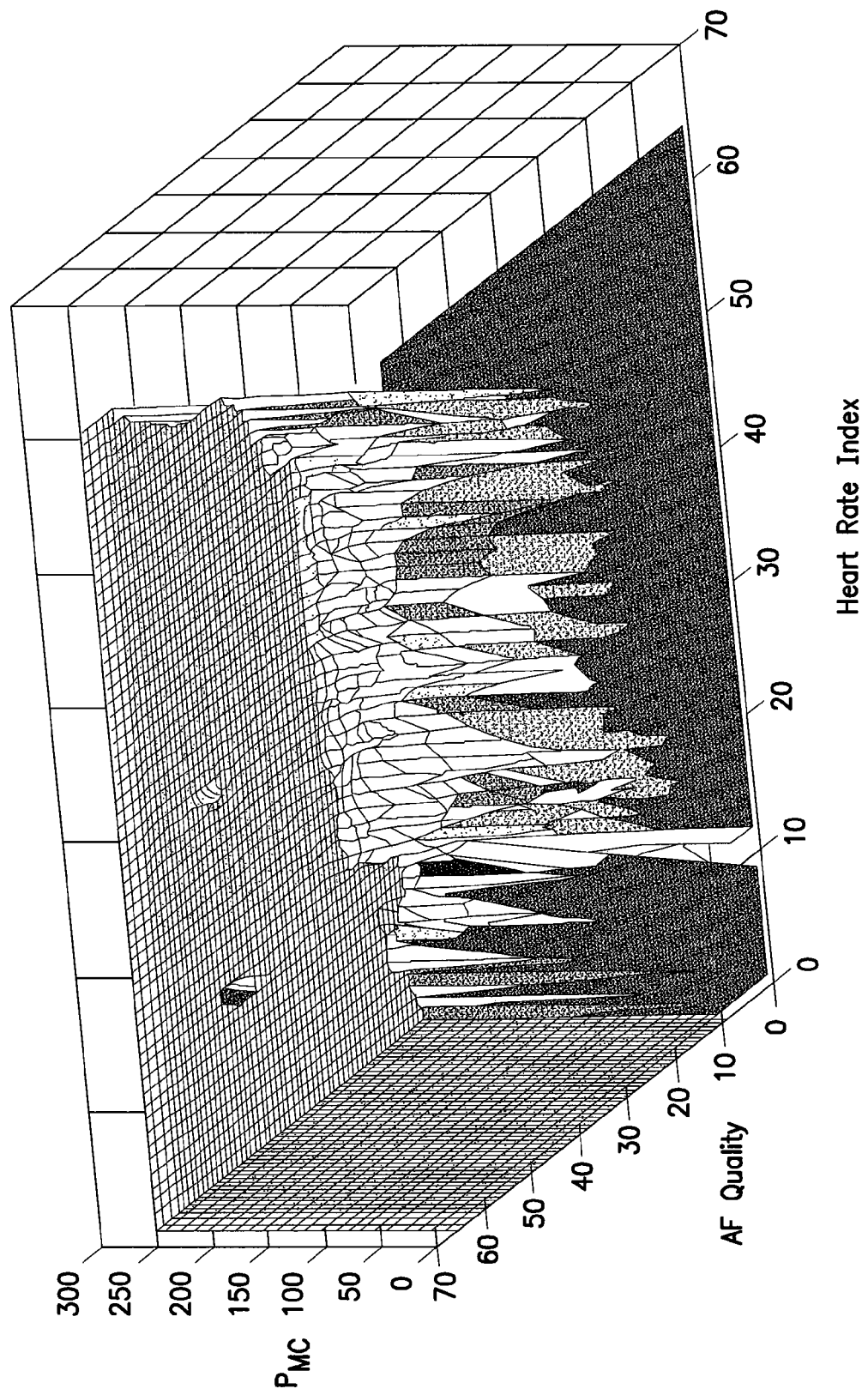
FIG. 4 is a graphic depiction of a lookup table relating AF quality and heart rate (expressed in terms of a heart rate index) and Markov-Chain probability ($P_{MC}$)

The above AF Quality equation is the same as Eq. 3, but with the addition of 1 to the numerator and denominator to avoid the possibility of a division by zero. This gives a result between 0 and infinity. The likelihood of AF is correlated to the AF Quality. As shown in FIG. 4, typically as the AF Quality increases, the likelihood of AF increases. However, as described above, AF Quality is one of two indexes into a probability map on the likelihood of AF. The other index is heart rate.

Further regarding AF Quality, since microcontrollers are fastest with integers, unlike numbers between 0 and 1 nor infinity, the algorithm maps this range into an integer range (a number between 0 and N). More specifically, to expand the numbers between 0 and 1 to integers, the top number is multiplied by a constant (usually 64 or 128 so it can be done with shifts) and if the result is larger than the size of the look up table, it is changed to a maximum value.

$$AF\ \text{Quality} = \frac{(\text{non } AF\ \text{distance} + 1) * \left(\frac{64}{\left(\frac{256/\text{number of } AF}{\text{Quality bins in lookup table}}\right)}\right)}{(AF\ \text{distance} + 1)} \quad (Eq.\ 5)$$

In the preceding example:

$$AF\ \text{Quality} = \frac{(12500 + 1) * \frac{64}{256/64}}{605 + 1} x = 106$$

Continuing with FIG. 9, at block 106, the algorithm calculates a heart rate index for the beat window, which is subsequently used in conjunction with the calculated AF Quality and a look-up table to determine the likelihood of AF, i.e., the Markov-Chain probability $P_{MC}$. A process of determining a heart rate index involves determining an average RR interval for the beat window corresponding to the beat window used to determine the AF Quality and mapping that average RR interval to an index based on the following:

$$\text{Average } RR\ \text{Interval} = \frac{\text{sum of } RR\ \text{bins}}{(dRR\ \text{window size} + 1)} \quad (Eq.\ 6)$$

$$\text{Heart rate index} = \frac{\text{Average } RR\ \text{interval} - 256}{\left(\frac{1024/\text{number of heart rate}}{\text{bins in lookup table}}\right)} \quad (Eq.\ 7)$$

Since it is an index into a table, the equation may change to reflect the size of the look up table. For instance if there is a valid range of 0 to 63, the division would change to 16 instead of 4, and the range would then be capped at 63 instead of 255. The size of the table may change, but there is some optimization potential to only do this calculation once per programmer.

As previously described, the Markov-Chain probability $P_{MC}$ is found with a multidimensional look up table. At block 107, with AF Quality and heart rate index as inputs to a look up table, a $P_{MC}$ for that bin transition and heart rate combination is found. In this example, the $P_{MC}$ would be represented as a number from 1 to 255 of the likelihood that that beat window of dRR values is AF. The higher the number, the more likely it is AF. A value of 128 indicates it is 50% probable it is AF.

Obtaining Variance Probability ($P_{VAR}$)

As described above, $P_{MC}$ is the first portion of the AF detection algorithm. The second portion is designed to try to avoid detecting bigeminy or trigeminy rhythms as AF. To do this, the algorithm calculates three variances and uses those values to look up the probability that it is AF.

The variances are calculated over a window of dRR values. One variance is calculated over all dRR values in the window, another is calculated over the negative dRR values and a third is calculated over the positive dRR values. The dRR window size used to determine variances is preferably different from the dRR window size used to determine $P_{MC}$. With reference to FIG. 11, in this example the dRR window size used to determine variance is 3, whereas the window size used to determine $P_{MC}$ is 9. The first 3 dRR values (not dRR bins) are 0, 1, −1.

Figure 17:
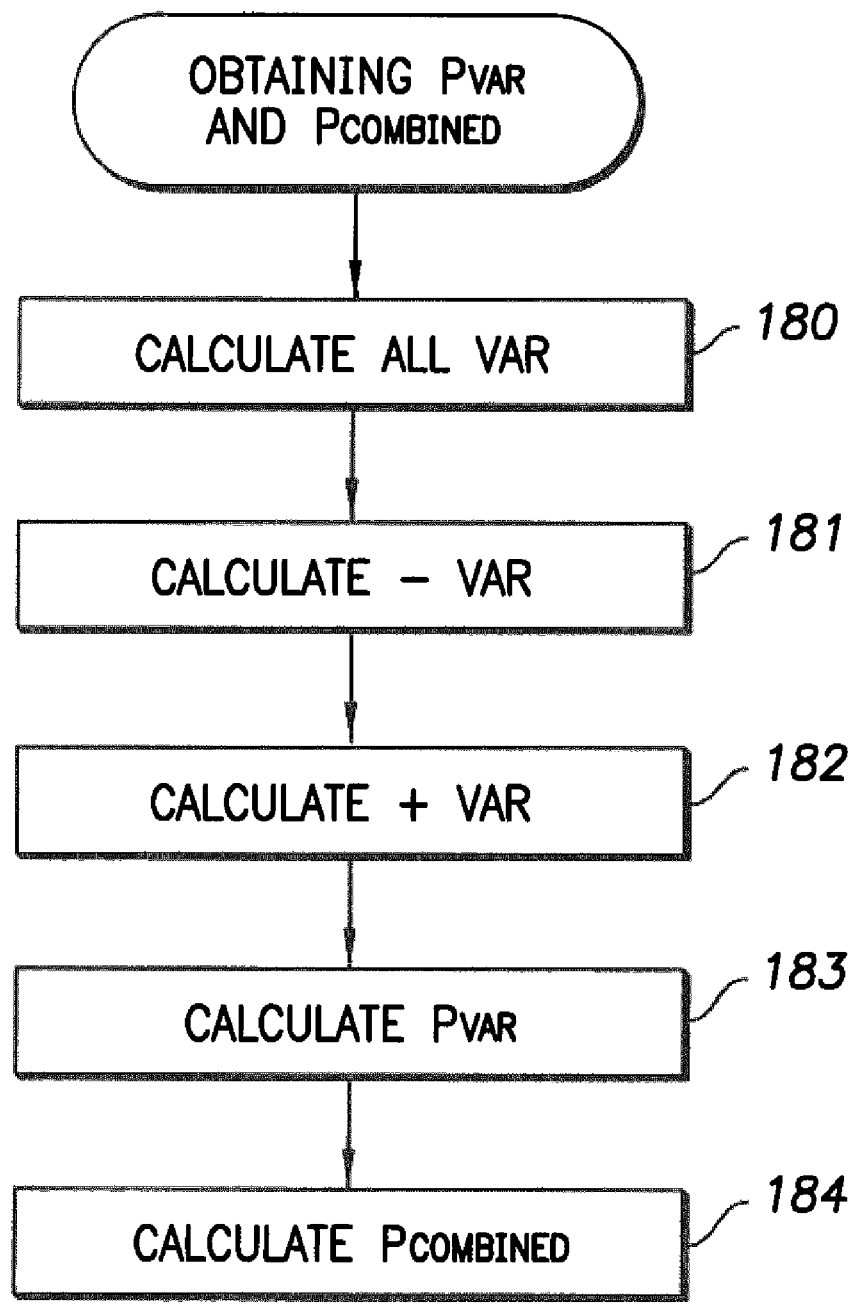
FIG. 17 is a flow chart illustrating a technique for obtaining variance probability ($P_{VAR}$) of AF.

With reference to FIG. 17, at block 180, a first variance (all Var) is calculated over all 3 dRR values.

Step 1. Calculate the Average (Integer Math):

$(0+1+(-1))/3=0$

Step 2. Add the square of the differences from the average together:

$(0-0)^2+(0-1)^2+(0-(-1))^2=2$

Step 3. Find the average of the square of the differences by dividing by the window size:

$2/3=1$

At block 181, a second variance (−Var) is calculated only over the negative dRR values.

Step 1. Calculate the Average (Integer Math):

$-1/1=-1$

Step 2. Add the square of the differences from the average together:

$(-1-(-1))^2=0$

Step 3. Find the average of the square of the differences by dividing by the number of the negative results:

$0/1=0$

At block 182, a third variance (+Var) is calculated only over the zero and positive dRR values Step 1. Calculate the Average (Integer Math):

$(0+1)/2=1$

Step 2. Add the square of the differences from the average together:

$(1-0)^2+(1-1)^2=1$

Step 3. Find the average of the square of the differences by dividing by the number of the negative results:

$1/2=1$

In this example the result is 1, 0, 1. But in the real world with larger windows the variances can get really large. Furthermore, the arithmetic performed by the device may be different in that 1 divided by 2 could be '0' instead of '1'. Accordingly, the variances may be converted to indexes using a division operation along with a capping action. Doing so maintains the variances within the table sizes.

All dRR Index=Min(All dRR Variance/dRR All Variance Divider,Number of All Variance Bins−1)

Negative dRR Index=Min(All dRR Variance/dRR Negative Variance Divider,Number of All Variance Bins−1)

Positive dRR Index=Min(All dRR Variance/dRR Positive Variance Divider,Number of All Variance Bins−1)

At block 183, using these three indexes, and another supplied look up table, the algorithm finds $P_{VAR}$, i.e., the probability that the combination of All Variance, Negative Variance and Positive Variations are AF.

At block 184, the algorithm combines $P_{MC}$ and $P_{VAR}$ using the following Bayesian inference equation to obtain an initial combined probability ($P_{COMBINED}$) which is used to determine if AF is onset. This equation is the same as Eq. 2, but the 1 has been replaced with 256 in order to map the probability between 0 and 256.

$$P_{COMBINED} = \frac{P_{MC} * P_{VAR} * 256}{P_{MC} * P_{VAR} + (256 - P_{MC}) * (256 - P_{VAR})} \quad (\text{Eq. 8})$$

Because of the use of integer math, the $P_{COMBINED}$ result provided by Eq. 8 may be further processed as follows to avoid a result of either 0 or 256:

$$P_{COMBINED} = \text{Max}(1, \text{Min}(255, P_{COMBINED(Eq.8)}))$$

This process sets $P_{COMBINED}$ to 1 in cases where $P_{COMBINED}$ from Eq. 8 is equal to 0, and to 255 in cases where $P_{COMBINED}$ from Eq. 8 is equal to 256.

For the given example, both the $P_{MC}$ and $P_{VAR}$ are sitting on the fence by replying that each indicates that it is 50% likely to be AF (a value of 128). Inputting these into the $P_{COMBINED}$ equation provides:

$$P_{COMBINED} = \frac{125 * 128 * 256}{128 * 128 + (256 - 128) * (256 - 128)}$$
$$= \frac{4194304}{(16384 + 16384)}$$
$$= 128$$

The resulting 128 or 50% indicates that the probability has not changed.

The next example looks at the scenario where $P_{MC}$ and $P_{VAR}$ disagree. If $P_{MC}$ indicates it is 95% likely to be AF, e.g., $P_{MC}$=243, and the $P_{VAR}$ look up indicates only 25% likely to be AF, e.g., $P_{VAR}$=64. In other words, $P_{VAR}$ thinks it is more likely to be Non AF than AF. In this case:

$$P_{COMBINED} = \frac{243 * 64 * 256}{243 * 64 + (256 - 243) * (256 - 64)}$$
$$= \frac{3981312}{(15552 + 2496)}$$
$$= 220$$

Now 220 is equivalent to an 85% probability (220/256) that is AF. The algorithm elegantly observed that $P_{MC}$ was much more confident that it was AF than $P_{VAR}$.

With reference to FIG. 6A, blocks 71 and 72, now that $P_{COMBINED}$ for the current beat window has been determined, the algorithm compares $P_{COMBINED}$ to a trigger threshold to detect AF onset. In this example, the trigger threshold may be 128, meaning that a $P_{COMBINED}$ greater than or equal to 128 indicates the presence of AF onset.

Once $P_{COMBINED}$ is found for the current beat window, the dRR window slides down one dRR to form the next beat window and proceeds with block 76 (or FIG. 6B, block 76', depending on the algorithm configuration). With reference to FIG. 18, that means the dRR window will now contain 6, 11, 5, 7 and the corresponding percentage chain for the bins instead of 11, 5, 7, 15 and their corresponding percentage chain.

Preferably however, in order to avoid repeating all of the preceding calculations for the new beat window, one large optimization may be implemented when sliding the window. Note that only two bin values changed, bin 6 and bin 15. Bin 6 changed because it was no longer in the window. Bin 15 changed because it just slid into the window. Also note that both slots changed by exactly the same amount, 25%. Since the window size is fixed, 1 count will always equal 25%. These observations can be exploited to make the distance calculations very microcontroller friendly. Since distance is simply the sum of the square of the differences, the individual bins can simply be updated. First it is necessary to subtract out the old square of the difference from bin 6, and add in the new square of the difference for 6. Doing the same for bin 15 and the distance calculation processing power no longer grows with the size of the dRR window.

New Distance=Old Distance−Removed Bin's Original Square of differences+Removed Bin's New Square of differences−New Bin's Original Square of differences+New Bin's New Square of differences Here is the example math for the Non AF Chain:

New Distance=12500−625+(0)2−0+(0−25)2=12500−625+0−0+625=12500

In summary, only updating the distances by the bin that slid out of the window and the bin that slid into the window will significantly reduce the computational power. Thus, after the initial window size is calculated, the window size does not affect the processing amount. As time (and thus the number of beats) approaches infinity, the average processing time per beat approaches the same constant regardless of the window size or the number of bins. The end result is that window size is not a significant factor in processing time and only influences memory requirements.

As the dRR window moves across the EGM stream, probabilities that the area under that window is AF are generated, but to improve results the preceding window probability is also used to update the probabilities of AF. This creates a level of hysteresis on the algorithm, and if the previous beats were AF, it is likely the next beats were also. As previously describe, a probability of AF for a current beat window is determined by combining $P_{COMBINED}$ for previous beat window, $P_{MC}$ for current beat window and $P_{VAR}$ for current beat window using Eq. 3. The very first window AF probability starts off at 50% (128), but as long as it is non-zero it will quickly stabilize due to the lossy nature of integer math.

It will be apparent from the foregoing that while particular forms of the invention have been illustrated and described, various modifications can be made without departing from the spirit and scope of the invention. For example, while the forgoing description has focused on AF detection by implantable monitoring devices, the principles of the invention may find application in other implantable cardiac rhythm management devices such as pacemakers, ICDs and CRT devices, as well as external devices, such as Holter monitors. Consequently, the specific structural and functional details disclosed herein are merely representative and do not limit the scope of the invention. The scope of the invention should be ascertained with reference to the claims.

What is claimed is:

1. A cardiac rhythm monitoring device comprising:
   electrodes adapted to be coupled to a patient to sense cardiac electrical activity; and
   a processor coupled to the electrodes to receive the electrical activity and programmed to detect ventricular events within the electrical activity, wherein a plurality of successive detected ventricular events define a first beat window; and for the first beat window:
      calculate RR intervals for each pair of adjacent ventricular events;
      calculate the differences (dRR) between successive RR intervals;
      determine a first probability of AF based on the presence of irregularity of the ventricular events, wherein to determine the first probability the programmer is further programmed to convert the dRR values into bin values based on a plurality of bin thresholds; calculate a transition measurement between successive bin values; calculate a sample chain of statistics using the transition measurements; compare the sample chain of statistics to a known AF chain of statistics and to a known non-AF chain of statistics; determine a measure of AF quality based on the comparisons; calculate a heart rate index based on the RR intervals; use a look-up table that correlates AF quality and heart rate index to a probability of AF to determine the first probability of AF;
      determine a second probability of AF based on variances of R-R intervals of the ventricular events, wherein to determine the second probability the programmer is further programmed to calculate a first variance over positive and negative dRR values; calculate a second variance only over the negative dRR values; calculate a third variance only over the positive dRR values; use a look-up table that correlates the first, second and third variances to a probability of AF to determine the second probability of AF; and
      combine the first and second probabilities of AF to obtain a first-beat-window combined probability of AF, wherein the combined probability of AF ranges between a minimum value and a maximum value;
      compare the combined probability of AF to an AF trigger threshold, wherein the AF trigger threshold is a predetermined value between the minimum value and the maximum value; and
      detect AF onset when the first-beat-window combined probability of AF is greater than or equal to the AF trigger threshold.

2. The device of claim 1 wherein a subsequent plurality of successive detected ventricular events define a subsequent beat window and the processor is further programmed to, upon detection of AF onset, determine a probability of AF for the subsequent beat window.

3. The device of claim 2 wherein to determine the probability of AF for the subsequent-beat-window AF probability, the processor is further programmed to, for the subsequent beat window:
   calculate RR intervals for each pair of adjacent ventricular events;
   calculate the differences (dRR) between successive RR intervals;
   determine a first probability of AF based on the presence of irregularity of the ventricular events within the subsequent beat window, wherein to determine the first probability the programmer is further programmed to convert the dRR values into bin values based on a plurality of bin thresholds; calculate a transition measurement between successive bin values; calculate a sample chain of statistics using the transition measurements; compare the sample chain of statistics to a known AF chain of statistics and to a known non-AF chain of statistics; determine a measure of AF quality based on the comparisons; calculate a heart rate index based on the RR intervals; use a look-up table that correlates AF quality and heart rate index to a probability of AF to determine the first probability of AF;
   determine a second probability of AF based on variances of R-R intervals of the ventricular events within the subsequent beat window, wherein to determine the second probability the programmer is further programmed to calculate a first variance over positive and negative dRR values; calculate a second variance only over the negative dRR values; calculate a third variance only over the positive dRR values; use a look-up table that correlates the first, second and third variances to a probability of AF to determine the second probability of AF; and
   combine the first and second probabilities of AF to obtain a subsequent-beat-window combined probability of AF.

4. The device of claim 3 wherein the processor is further programmed to:
   compare the subsequent-beat-window combined probability of AF to the AF trigger threshold;
   confirm AF onset if the subsequent-beat-window combined probability of AF is greater than or equal to the AF trigger threshold; and
   detect AF termination when the subsequent-beat-window combined probability of AF is less than the AF trigger threshold.

5. The device of claim 2 wherein to determine the subsequent-beat-window AF probability, the processor is further programmed to:
   determine a probability of AF based on the presence of irregularity of the ventricular events within the subsequent beat window, wherein to determine the probability the programmer is further programmed to convert the dRR values into bin values based on a plurality of bin thresholds; calculate a transition measurement between successive bin values; calculate a sample chain of statistics using the transition measurements; compare the sample chain of statistics to a known AF chain of statistics and to a known non-AF chain of statistics; determine a measure of AF quality based on the comparisons; calculate a heart rate index based on the RR intervals; use a look-up table that correlates AF quality and heart rate index to a probability of AF to determine the probability of AF.

6. The device of claim 5 wherein the processor is further programmed to:
   compare the subsequent-beat-window AF probability to a predetermined threshold indicative of AF;
   confirm AF onset if the subsequent-beat-window AF probability is greater than or equal to the predetermined threshold; and
   detect AF termination if the subsequent-beat-window AF probability is less than the AF trigger threshold.

7. The device of claim 2 wherein the subsequent beat window comprises a first beat corresponding to the beat subsequent to the first beat of the first beat window and a last beat corresponding to a beat subsequent to the last beat of the first beat window.

8. The device of claim 4 wherein the processor is programmed to detect AF onset when the first-beat-window AF probability and each of a plurality of consecutive subsequent-beat-window AF probabilities are greater than or equal to the AF trigger threshold; and detect AF termination when each of a plurality of consecutive subsequent-beat-window AF probabilities are less than the trigger threshold.

9. A method of detecting atrial fibrillation comprising:

detecting electrical activity using electrodes adapted to be coupled to a patient;

detecting ventricular events within electrical cardiac activity using a processor, wherein a plurality of successive detected ventricular events define a first beat window;

for the first beat window, performing the following using the processor:

calculating RR intervals for each pair of adjacent ventricular events;

calculating the differences (dRR) between successive RR intervals;

determining a first probability of AF based on the presence of irregularity of the ventricular events by: converting the dRR values into bin values based on a plurality of bin thresholds; calculating a transition measurement between successive bin values; calculating a sample chain of statistics using the transition measurements; comparing the sample chain of statistics to a known AF chain of statistics and to a known non-AF chain of statistics; determining a measure of AF quality based on the comparisons; calculating a heart rate index based on the RR intervals; using a look-up table that correlates AF quality and heart rate index to a probability of AF to determine the first probability of AF;

determining a second probability of AF based on variances of R-R intervals of the ventricular events by: calculating a first variance over positive and negative dRR values; calculating a second variance only over the negative dRR values; calculating a third variance only over the positive dRR values; using a look-up table that correlates the first, second, and third variances to a probability of AF to determine the second probability of AF; and combining the first and second probabilities of AF to obtain a first-beat-window combine probability of AF, wherein the combined probability of AF ranges between a minimum value and a maximum value; and determining AF onset when the first-beat-window combined probability of AF is greater than or equal to the AF trigger threshold.

10. The method of claim 9 wherein combining is performed using a Bayesian inference equation.

* * * * *